United States Patent
Knight et al.

(10) Patent No.: US 12,378,177 B2
(45) Date of Patent: Aug. 5, 2025

(54) REDUCING ENERGY CONSUMPTION IN MEG RECLAMATION

(71) Applicant: Schlumberger Technology Corporation, Sugar Land, TX (US)

(72) Inventors: David John Knight, Gatwick (GB); Steven Langley, Gatwick (GB); Bryan Bussell, Sutton (GB)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 655 days.

(21) Appl. No.: 17/756,449

(22) PCT Filed: Dec. 1, 2020

(86) PCT No.: PCT/US2020/062701
§ 371 (c)(1),
(2) Date: May 25, 2022

(87) PCT Pub. No.: WO2021/113236
PCT Pub. Date: Jun. 10, 2021

(65) Prior Publication Data
US 2023/0002298 A1    Jan. 5, 2023

Related U.S. Application Data

(60) Provisional application No. 62/942,489, filed on Dec. 2, 2019.

(51) Int. Cl.
*C07C 29/80*   (2006.01)
*B01D 1/00*    (2006.01)
*B01D 1/28*    (2006.01)

(52) U.S. Cl.
CPC ............ *C07C 29/80* (2013.01); *B01D 1/0041* (2013.01); *B01D 1/2856* (2013.01)

(58) Field of Classification Search
CPC ..... C07C 29/80; C07C 31/202; B01D 1/0041; B01D 1/2856
See application file for complete search history.

(56) References Cited

U.S. PATENT DOCUMENTS 4,182,659 A    1/1980  Anwer et al.
6,120,651 A    9/2000  Gammon et al.
(Continued)

FOREIGN PATENT DOCUMENTS

CN    102794136 A    11/2012
CN    103232312 A    8/2013
(Continued)

OTHER PUBLICATIONS

ZLD Crystallizer For Wastewater Treatment, downloaded on May 15, 2022 from https://www.suezwatertechnologies.com/products/evaporators-crystallizers/crystallizers (2 pages).
(Continued)

*Primary Examiner* — Jafar F Parsa
(74) *Attorney, Agent, or Firm* — Jeffrey D. Frantz

(57) ABSTRACT

A method is described herein, comprising vaporizing a glycol material by thermal contact with a heating medium to form a vaporized glycol stream, increasing a pressure of the vaporized glycol stream to form a pressurized glycol stream, and increasing a temperature of the heating medium by thermally contacting the heating medium with the pressurized glycol stream.

19 Claims, 3 Drawing Sheets

(56) References Cited

U.S. PATENT DOCUMENTS

| | | |
|---|---|---|
| 8,728,321 B2 | 5/2014 | Nazzer |
| 2009/0277770 A1 | 11/2009 | Malatesta |
| 2015/0047965 A1 | 2/2015 | Malatesta |
| 2017/0015613 A1 | 1/2017 | King et al. |
| 2017/0368469 A1 | 12/2017 | Zheng et al. |

FOREIGN PATENT DOCUMENTS

| | | | |
|---|---|---|---|
| CN | 103626656 A | 3/2014 | |
| JP | H04313302 A | 11/1992 | |
| JP | H05237302 A | 9/1993 | |
| KR | 1020170059675 A | 5/2017 | |
| KR | 101795003 B1 | 11/2017 | |
| KR | 1020190125637 A | 11/2019 | |
| WO | 9601678 A1 | 1/1996 | |
| WO | 2007073204 A1 | 6/2007 | |
| WO | WO-2010080038 A1 * | 7/2010 | ............. C07C 29/86 |
| WO | 2017064036 A1 | 4/2017 | |

OTHER PUBLICATIONS

Forced Circulation Vacuum Evaporators, downloaded on May 15, 2022 from https://condorchem.com/en/forced-circulation-vacuum-evaporators/ (7 pages).

Industrial Process Equipment Supplier _ Sunkaier, downloaded on May 15, 2022 from http://www.sunkaier.com/products/evaporation-crystallization/evaporator/falling-film-evaporation-with-mvr/ (6 pages).

Evaporation Technology, downloaded on 05116/22 from https://files.vogel.de/vogelonline/vogelonline/companyfiles/10852.pdf (16 pages).

Carbon Dioxide Emissions Coefficients, downloaded on May 15, 2022 from https://www.eia.gov/environment/emissions/co2_vol_mass.php (2 pages).

International Search Report and Written Opinion issued in PCT Application PCT/US2020/062701, dated Mar. 24, 2021 (9 pages).

* cited by examiner

REDUCING ENERGY CONSUMPTION IN MEG RECLAMATION

CROSS-REFERENCE TO RELATED APPLICATION

The present document is a National Stage Entry of International Application No. PCT/US2020/062701, filed Dec. 1, 2020, which is based on and claims priority to U.S. Provisional Application Ser. No. 62/942,489, filed Dec. 2, 2019, which is incorporated herein by reference in its entirety.

FIELD

Embodiments herein generally relate to apparatus and methods for reclaiming monoethylene glycol (MEG), or other glycols, in oil and gas processing. Specifically, methods and apparatus are described herein for reducing energy consumption in MEG reclamation.

BACKGROUND

Glycols are used in oil and gas recovery to suppress formation of gas hydrate crystals, which can negatively impact production and transportation of hydrocarbon products. The glycols are expensive, so reclamation and reuse of glycols is common in such processes. Among other processes, glycols, and specifically monoethylene glycol (MEG), are thermodynamically separated from other materials through application of thermal energy, for example in a distillation process. There is a continuing need to reduce the energy applied in reclamation of glycols, and specifically MEG, in oil and gas processing.

SUMMARY

Embodiments described herein provide a method, comprising vaporizing a glycol material by thermal contact with a heating medium to form a vaporized stream; increasing a pressure of the vaporized stream to form a pressurized vapor stream; and increasing a temperature of the heating medium by thermally contacting the heating medium with the pressurized stream.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
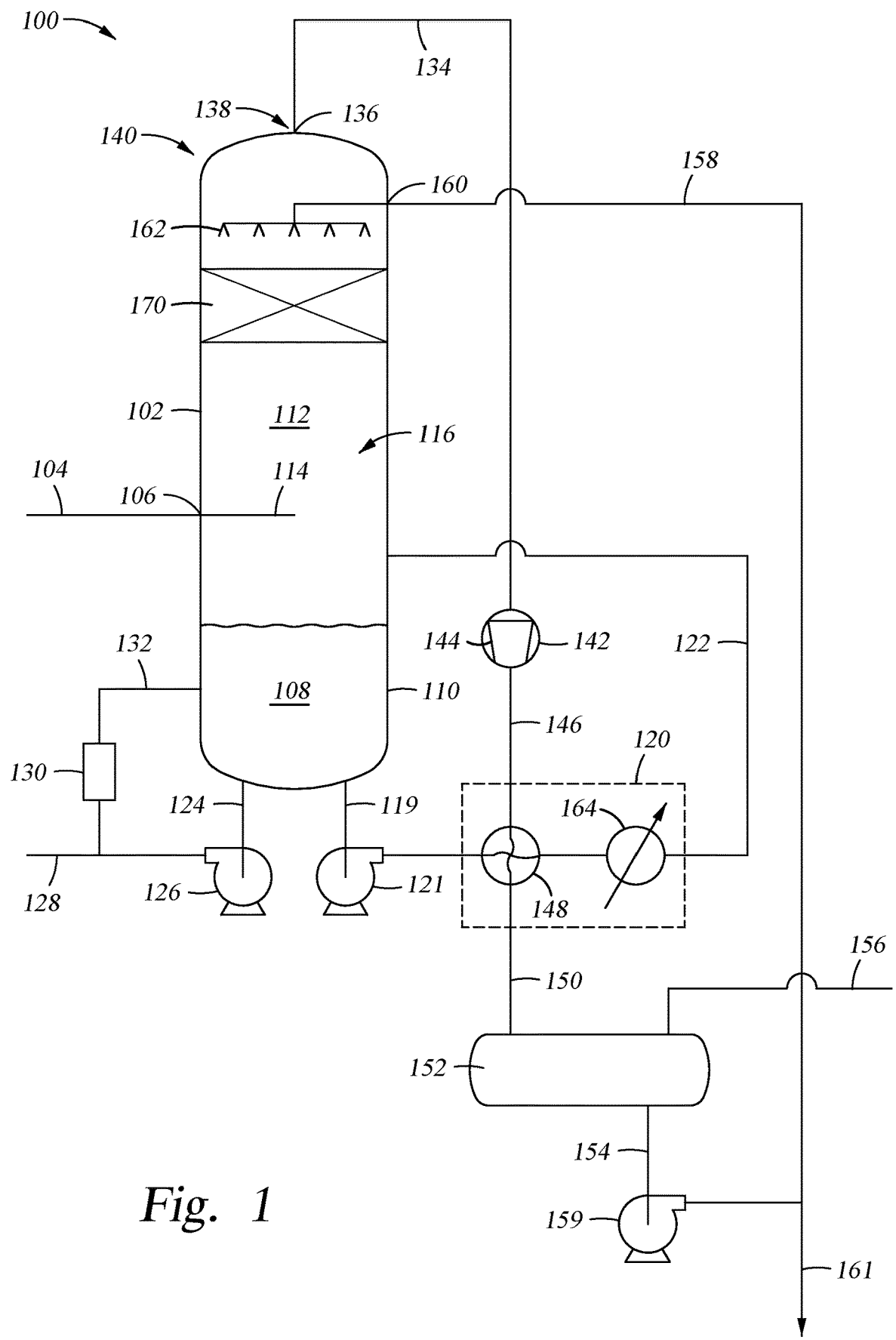
FIG. 1 is a schematic process view of a glycol reclamation process 100 according to one embodiment.

FIG. 1 is a schematic process view of a glycol reclamation process 100 according to one embodiment. The process 100 uses a vaporizer 102 to vaporize glycol from a feed stream 104. The feed stream 104 is provided to the vaporizer 102 at a feed location 106. A liquid phase 108 is maintained inside the vaporizer 102. The feed location 106 is a port through a sidewall 110 of the vaporizer 102. The feed stream 104 may flow through the feed location 106 into the liquid phase 108, or, as here, the feed stream 104 may flow through the feed location 106 into a vapor phase 112 located above the liquid phase 108. In some cases, as shown here, an optional delivery conduit 114 may extend from the feed location 106 into an interior 116 of the vaporizer 102, such that the feed stream 104 flows to a location in the interior 116 that is spaced apart from the sidewall 110.

The feed stream 104 contains glycol, for example MEG, from an oil and gas processing facility. The feed stream 104 typically also contains water and potentially other solid and liquid components. The liquid phase 108 is maintained at a temperature that vaporizes at least a portion of the glycol from the feed stream 104. In the case of a feed stream containing MEG and water, the liquid phase 108 is maintained at a temperature that heats at least a portion of the feed stream to a temperature between the vaporization temperature of MEG and water, at an operating pressure of the vaporizer 102, and a degradation temperature of MEG. Pressure of the vaporizer 102 is maintained such that the vaporization temperature of the glycol is less than a degradation temperature of the glycol.

The glycol, and potentially some water, is vaporized by thermal contact with a heating medium in the vaporizer 102. The heating medium may be the liquid of the liquid phase 108, or may be separated from the liquid phase 108 by a thermal contact structure, such as a heat exchanger or thermal coil. In some cases the heating medium is a material that is immiscible with glycol, such as a hydrocarbon material. In other cases, the heating medium may be a concentrated glycol material. A portion of the heating medium is withdrawn from the vaporizer 102 through a withdrawal line 119 and routed to a thermal section 120, optionally using a recycle pump 121. The thermal section 120 increases a temperature of the heating medium to a temperature that supports vaporization of glycol in the vaporizer 102. The heating medium is routed from the thermal section 120 back to the vaporizer 102 through a recycle line 122. Dissolved materials in the feed stream 104 can precipitate in the liquid phase 108 as vapor leaves the liquid phase 108 and enters the vapor phase 112. Buildup of these solids can be managed by withdrawing a purge portion of the liquid phase 108 through a purge line 124, optionally using a purge pump 126. The purge portion can be routed to disposal through a disposal line 128, or can optionally be routed to a remediation section 130 that removes some or all of the solids to form a cleaned heating medium. The cleaned heating medium can then be routed back to the vaporizer 102 through a clean line 132. The remediation section 130 can feature any solids removal unit, or combination thereof, including centrifuges, hydrocyclones, filters, settlers, and the like.

Vapor evaporated in the vaporizer 102 enters the vapor phase 112, which is withdrawn from the vaporizer as a vaporized stream through a vapor line 134 coupled to the vaporizer 102 at a vapor withdrawal location 136, which may be located at a top 138 of the vaporizer 102 or in an upper portion 140 of the vaporizer 102. The vapor line 134 is coupled to a pressurizing unit 142 that increases a pressure of the vapor in the vapor line 134. The pressurizing unit 142 may include a compressor 144 to compress all of, or part of, the vapor in the vapor line 134. Pressurizing the vaporized stream in the vapor line raises the vapor pressure of components in the vapor line 134, thus forming a pressurized stream having a dew point temperature higher than the vaporized stream. The vaporized stream is pressurized to an extent that the dew point temperature of the pressurized stream is above the temperature of the heating medium entering the thermal section 120. The pressurized stream is routed through a pressurized line 146 to the thermal section 120.

Using a thermal contactor 148, the pressurized stream is thermally contacted with the heating medium routed to the thermal section 120. The thermal contactor 148 may be a heat exchanger of any useful type, such as a plate exchanger, a shell and tube exchanger, a spiral plate exchanger, a wide-gap exchanger, a falling film tube exchanger, or other type of exchanger. In some embodiments, a scale resistant exchanger design can be helpful in this service. The heating medium is at a temperature, upon entering the thermal contactor 148, that results in thermal energy flowing from the pressurized stream to the heating medium. The thermal energy is extracted from the pressurized stream mostly as latent heat, so that at least a portion of the pressurized stream condenses in the thermal contactor 148, forming an extracted stream that exits the thermal contactor 148 through an extracted stream conduit 150. The extracted stream conduit 150 is coupled to a phase separator 152, where liquid is withdrawn through a condensate line 154 and vapor is withdrawn through a reduced vapor line 156, which can be routed to further processing such as glycol purification.

The condensate can be returned to the vaporizer 102 through a condensate return line 158, optionally using a condensate pump 159. Condensate can also be withdrawn or purged using a condensate withdrawal line 161. The condensate return line 158 enters the vaporizer 102 at a condensate return location 160 of the sidewall 110 that may be located in the liquid phase 108 or the vapor phase 112 of the vaporizer 102. In this case, the condensate return location 160 is in the vapor phase 112, and the condensate return line 158 extends to a central region of the vaporizer 102 and couples to a distributor 162. The distributor 162 distributes the condensate as droplets in the interior 116 of the vaporizer 102 to scavenge particles and droplets of the heating medium that might entrain in the vapor phase 112. Droplets of condensate travel downward through the vapor phase 112, interacting with droplets of heating medium and other entrained liquids, encouraging the entrained liquids downward to the liquid phase 108. A surface area structure 170, which may be any convenient type of packing or tray structure, can optionally be used to increase the area of contact between downgoing condensate and upgoing vapor and entrained liquid droplets to increase removal of small liquid droplets in the vapor stream. Returning condensate to the vaporizer 102 in this way reduces entrainment of liquid in the vapor exiting the vaporizer 102. Liquid from the heating medium that might emerge in the vaporized stream 134 will be returned to the vaporizer 102 with the condensate. It should be noted that the feed stream 104 may also be charged to the vaporizer 102 in a similar way, by spraying the liquid feed stream into the upgoing vapor of the vapor phase 112 to further reduce entrained liquid droplets.

A temperature of the heating medium is increased in the thermal contactor 148. The thermal section 120 generally increases the temperature of the heating medium to a temperature selected to vaporize glycol in the vaporizer 102. Since the heating medium flows from the thermal section 120 back to the vaporizer 102, enduring some heat loss along the way, the temperature of the heating medium upon leaving the thermal section 120 is selected such that the temperature of the heating medium upon re-entering the vaporizer 102 is such that glycol is vaporized in the vaporizer 102. If necessary, a heater 164 can be provided in the thermal section 120 to achieve a target temperature of the heating medium. The pressurizing unit 142 and the heater 164 can be used together to optimize energy input to the heating medium to achieve the desired temperature therein. Depending on the composition of the vaporized stream, more or less latent heat may be available in the vaporized stream. Additional energy needed to achieve the target temperature of the heating medium can be obtained using the heater 164.

The glycol reclamation process 100 is controlled to maximize glycol recovery per unit energy consumption. Temperature of the heating medium returned to the vaporizer 102 is measured, and the pressurizing unit 142 and the heater 164 are adjusted to maintain the recycled heating medium temperature. In one case, duty of the heater 164 is adjusted to maintain the recycled heating medium temperature, and pressurizing unit duty is then used to minimize energy consumption. Duty of the pressurizing unit 142 will directly affect flow rate of condensate 154, and will inversely affect flow rate of reduced vapor 156. The more condensate formed, the more latent heat is used to heat the heating medium, and the less additional energy added using the heater 164. If an increment of energy used to create one degree of heating using latent heat is less than achieving the same degree of heating using the heater 164, pressurizing duty should be increased until the marginal energy for each unit is the same. Likewise, if an increment of energy used to create one degree of heating using the heater 164 is less than achieving the same degree of heating using latent heat, pressurizing duty should be decreased until the marginal energy for each unit is the same. In one case, energy consumption of the pressurizing unit 142 and the heater 164 can be directly measured, duty of the pressurizing unit 142 can be adjusted by a small increment, and the control response of the heater 164 determined. The overall change in energy consumption can then be evaluated to determine whether the new operating state consumes less energy than the old operating state. Such manipulations can be repeated, increasing or decreasing the pressurizing unit duty to seek an optimum. In another case, pressurizing unit duty can be adjusted based on recycled heating medium temperature, and heat input using the heater 164 can be manipulated to reduce overall energy consumption. Simulators can also be used to predict the effect of changes in pressurizing unit duty or heater input, by measuring composition of the vaporized stream and simulating the latent heat available in the stream and its effect on temperature of the heating medium.

Figure 2:
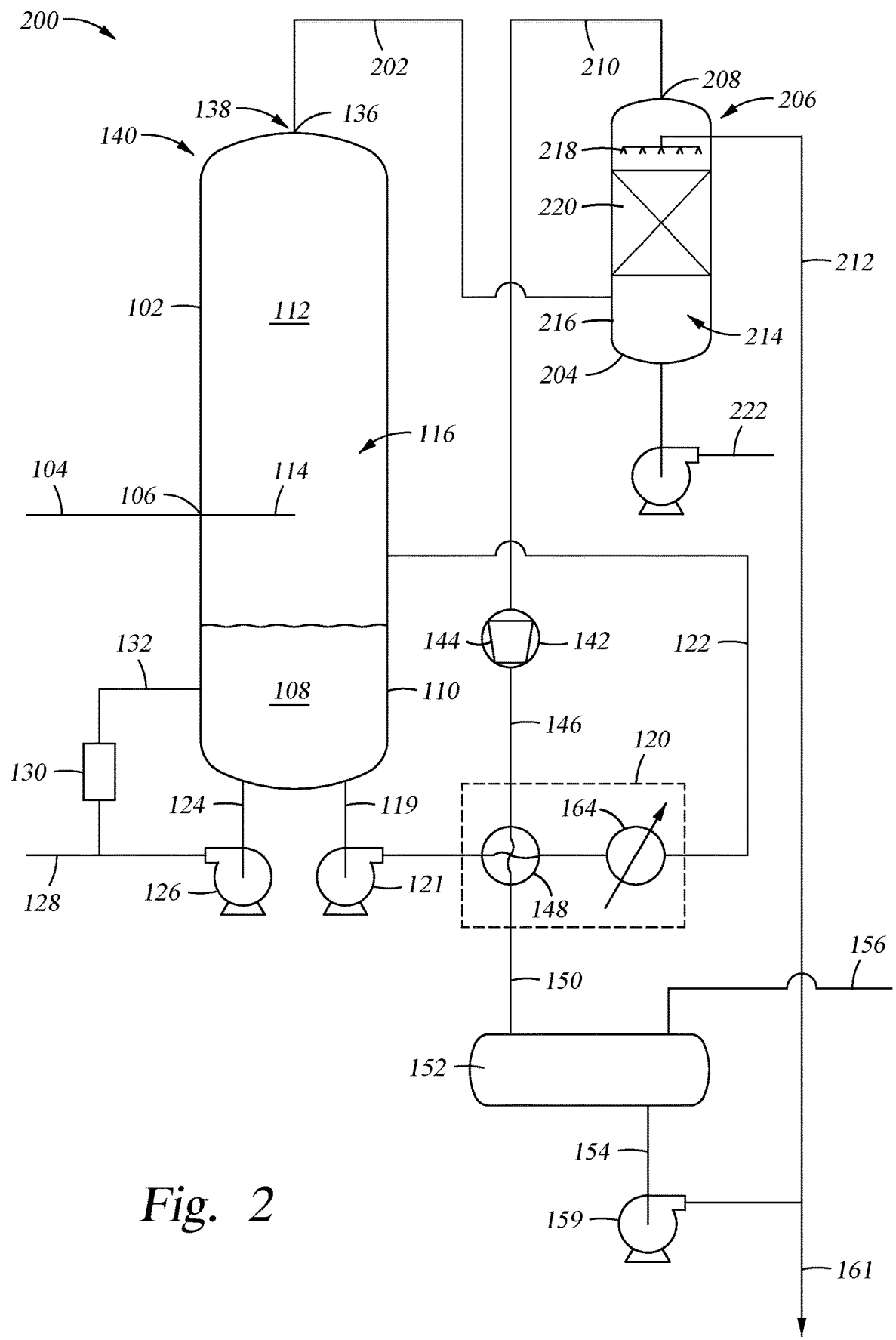
FIG. 2 is a flow diagram summarizing a method according to another embodiment.

FIG. 2 is a schematic process view of a glycol reclamation process 200 according to another embodiment. In the embodiment of FIG. 2, a vaporized stream 202 is recovered from the vaporizer 102 at the vapor withdrawal location 136 and routed to a treater 204, which may be a distillation column. A treated vapor stream exits from an upper region 206 of the treater 204, in some cases the top 208 of the treater 204, and is the routed to the pressurizing unit 142 by a treated vapor line 210. The treated vapor stream may be a purified glycol stream that has been reduced in water content. A condensate line 212 routes all or a portion of the condensate from the phase separator 152 to the upper region 206 of the treater 204. In this case, the condensate line 212 extends to an interior 214 of the treater 204, through a sidewall 216 thereof to couple to a distributor 218. In this case, a surface area structure 220, which may be any of the types of surface area structures listed above in connection with FIG. 1, is disposed in the treater 204 to enhance the process performed by the treater 204. In one case, the surface area structure 220 may aid in mass transfer for a distillation process. Downgoing liquid exits the treater 204 at a bottom of the treater 204 through a bottoms line 222. The bottoms line 222 is not shown directed to any particular use in FIG. 2, but may be recycled back to the vaporizer 102, recovered as lean glycol product, or routed to disposal or further processing elsewhere. The bottoms in the bottoms line 222 may be mixed with reduced vapor 156, if desired, for routing to further glycol purification.

In this embodiment, overall evaporative load on the vaporizer 102 is reduced because less glycol containing material is recycled to the vaporizer 102 relative to the embodiment of FIG. 1. Instead of recycling condensate into the vaporizer, the condensate is recycled to the scrubber 204 and then routed to further processing.

Figure 3:
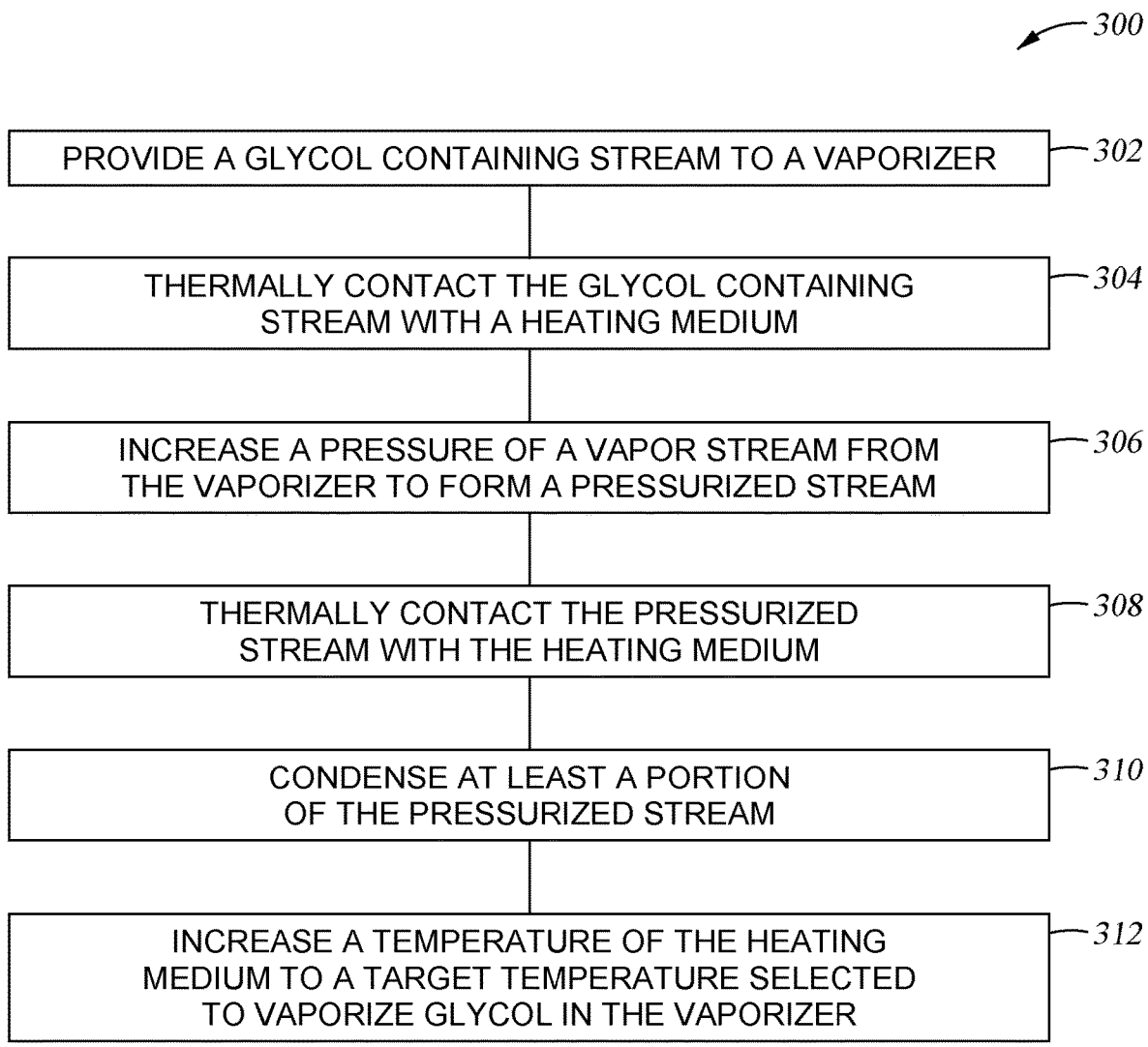
FIG. 3 is a flow diagram summarizing a method according to yet another embodiment.

FIG. 3 is a flow diagram summarizing a method 300 according to one embodiment. The method 300 is a method of recovering glycol from a mixture. The mixture may be a glycol containing stream from an oil and/or gas processing facility. In many situations, the glycol is MEG, and the glycol containing stream also has water and solids. At 302, the glycol containing stream is provided to a vaporizer. The vaporizer is a vessel for applying thermal energy to the glycol containing stream to vaporize glycol, and in some cases water or other light materials, from the glycol containing stream.

At 304, the glycol containing stream is thermally contacted with a heating medium to form a vaporized stream. Thermal energy is transmitted from the heating medium to the glycol containing stream to vaporize glycol, and in some cases water, from the glycol containing stream to form the vaporized stream. The glycol containing stream may directly contact the heating medium in a liquid pool of the heating medium with unvaporized components from the glycol containing stream, or the thermal contact may be mediated by a thermal contact structure, such as a heat exchanger. The heating medium is maintained at a vaporization temperature selected to vaporize glycol from the glycol containing stream or from the liquid pool without substantially degrading the glycol.

The heating medium may be any material that can be heated and can transmit heat to another material. The material may be in direct contact with the glycol containing stream in the vaporizer, so a material that is immiscible, or only partially miscible with glycol can be used. The material can also be miscible with glycol, but azeotrope formation should be avoided. Hydrocarbon materials can be used, and are immiscible with most glycols, including MEG. The hydrocarbon materials generally have a boiling point significantly higher than the glycol to be recovered.

At 306, a pressure of the vaporized stream is increased to form a pressurized stream. All or a portion of the vaporized stream can be compressed using any suitable compressor, rotating or reciprocating. A portion of the vaporized stream may be obtained by simple flow separation, or the portion of the vaporized stream may be obtained by a process, such as distillation, flashing, or extraction performed on the vaporized stream to yield a portion thereof. For example, a distillation process performed on the vaporized stream may yield a portion of the vaporized stream as overhead, which portion can be increased in pressure and used subsequently in the method 300.

The pressure of the vaporized stream, or portion thereof, is increased to raise the vapor pressure of components of the stream such that the pressurized stream will have a temperature to support heat transfer to the heating medium. Thus, the vaporized stream, or portion thereof, is pressurized to a pressure that yields a target temperature for heating the heating medium. The pressurization can be essentially adiabatic or sub-adiabatic. In this context, sub-adiabatic pressurization is a pressurization process that yields a temperature rise less than the temperature rise that an adiabatic pressurization would yield due to thermal losses. The pressurized stream is brought to a thermodynamic state that is mainly, or completely, gas phase with a temperature at or above the dew point of the pressurized stream, but near enough to the dew point of the stream that reducing the temperature of the stream by thermal contact with a cooler stream will result in some condensation of the pressurized stream, and accompanying release of latent heat. In some cases, the pressurized stream may be de-superheated.

In some embodiments, flow rate and thermal condition of the pressurized stream may be selected to maximize transferrable thermal energy to the heating medium. A controller can monitor composition of the vaporized stream formed at 304, or a portion of the vaporized stream derived from other processing. The controller can use a thermodynamic model to determine the conditions for deriving maximum transferrable thermal energy from any such streams, and can manipulate control valves to deliver a flow rate of a selected composition to be pressurized to a selected pressure using a controllable compressor. Depending on available mass and composition, a slip stream of the vaporized stream can be routed to the compressor, or a distilled overhead stream can be routed to the compressor, or a mixture of the two. The controller can also adjust circulation rate of the heating medium and other variables to maximize or optimize recovery of thermal energy from the vaporized stream.

Adjusting thermal condition of the pressurized stream includes adjusting temperature and/or pressure. In some cases, one or both of temperature and pressure may be adjusted to move the thermal condition of the pressurized stream to a state that maximizes available transferrable thermal energy. For example, where increasing pressure to form the pressurized stream produces a small amount of condensate, the pressurized stream can be heated using a trim heater to vaporize the condensate. Alternately, or additionally, compressor duty can be reduced to avoid condensation. In other cases, a trim cooler can be used to de-superheat the pressurized stream, or even to subcool the pressurized stream in some cases.

At 308, the pressurized stream is thermally contacted with the heating medium. A portion of the heating medium is withdrawn from the vaporizer and routed to a thermal contactor. The pressurized stream is also routed to the thermal contactor, where thermal exchange occurs between the pressurized stream and the heating medium. The thermal contactor is typically an apparatus that provides a thermally conductive interface between the pressurized stream and the heating medium. One or more metal walls may contact both the pressurized stream and the heating medium to facilitate flow of thermal energy from the pressurized stream to the heating medium.

At 310, the flow of thermal energy from the pressurized stream to the heating medium condenses at least a portion of the pressurized stream. The condensed portion of the pressurized stream can be separated from the non-condensed portion, if desired, and the condensed portion can be returned to the vaporizer or routed to other processing.

At 312, a temperature of the heating medium is increased to a target temperature selected to vaporize at least a portion of the glycol in the vaporizer. A second heater may be used to achieve the target temperature. The temperature of the heating medium is initially increased by thermal contact with the pressurized stream, and processing in the second heater brings the temperature to the target. The heating medium is then routed back to the vaporizer.

In one embodiment, MEG and water are vaporized in a vaporizer. The MEG and water are brought into direct contact with a heating medium that is immiscible with MEG. The heating medium in the vaporizer is maintained at a vaporization temperature that is between a boiling temperature of MEG and a boiling temperature of water. In some cases, the vaporizer is operated under reduced pressure so that the heating medium can be maintained at a lower temperature. Maintaining the heating medium at a lower temperature to vaporize MEG can reduce degradation rate of the MEG.

The MEG/water vapor is taken overhead in the vaporizer and routed to a compressor. The compressor boosts the pressure of the MEG/water vapor substantially adiabatically, raising the temperature of the MEG/water vapor along, or near, a saturation limit. Meanwhile, a portion of the heating medium is withdrawn from the vaporizer and routed to a thermal contactor. Upon entering the thermal contactor, the heating medium is at an inlet temperature that may be below the temperature of the heating medium in the vaporizer due to thermal losses. The compression of the MEG/water vapor is configured to raise the temperature of the MEG/water vapor to a level at or above the inlet temperature of the heating medium. The compressed MEG/water vapor is then routed to the thermal contactor to heat the heating medium. The compressed MEG/water vapor is cooled somewhat in the thermal contactor and caused to condense, at least partially. The heat released by the condensation heats the heating medium to an outlet temperature at the thermal contactor. The heating medium is then optionally routed to a trim heater that raises the temperature of the heating medium to a target temperature such that the heating medium is maintained at the vaporization temperature.

The cooled MEG/water stream is routed to a settler to separate vapor from liquid. The liquid may be routed back to the vaporizer for further purification, or may be sent on to subsequent purification operations. The vapor is also typically routed to subsequent purification operations. In this way, heat of vaporization added to the MEG/water vapor is at least partially recovered into the heating medium to conserve energy.

Use of latent heat to heat the heating medium can generally be maximized by measuring flow rates of reduced vapor and condensate after the MEG/water stream is cooled. Maximizing condensate maximizes use of latent heat, but incremental compression duty to achieve incremental condensation may take more energy to heat the heating medium than using the trim heater. Energy consumption by a compressor can be directly measured by measuring electrical current to the compressor. Energy consumption by the trim heater can be measured by measuring inlet and outlet temperatures, and flow rate, of thermal fluid used in the trim heater, or by measuring current if the trim heater is electrical. In any case, marginal changes in energy consumption by the compressor and by the trim heater can be compared to determine whether to increase compressor duty to capture more latent heat. Compressor duty or trim heating can then be adjusted. The component that is not adjusted can be slaved to temperature of the heating medium so that as compression duty is increased, trim heating will automatically decrease, and vice versa.

While the foregoing is directed to embodiments of the subject matter of this disclosure, other and further embodiments of the present disclosure may be devised without departing from the basic scope thereof, and the scope thereof is determined by the claims that follow.

What is claimed is:

1. A method, comprising:
vaporizing, in a vaporizer, a first liquid via heat transfer from a second liquid to form a vaporized stream that exits the vaporizer, the vaporized stream including monoethylene glycol (MEG);
increasing a pressure of at least a portion of the vaporized stream to form a pressurized vapor stream;
withdrawing a portion of the second liquid from the vaporizer;
increasing a temperature of the portion of the second liquid by transferring heat from the pressurized vapor stream to the portion of the second liquid without mixing the pressurized vapor stream with the portion of the second liquid; and
returning the portion of the second liquid to the vaporizer after the increasing of the temperature of the portion of the second liquid.

2. The method of claim 1, wherein the heat is transferred from the pressurized vapor stream to the portion of the second liquid via a thermal contactor, and at least a portion of the pressurized vapor stream condenses in the thermal contactor during the transfer of the heat.

3. The method of claim 1, wherein the at least a portion of the vaporized stream is a distillation overhead stream.

4. The method of claim 1, wherein the increasing the pressure of the at least a portion of the vaporized stream includes:
treating the vaporized stream to form a treated stream; and
compressing the treated stream.

5. The method of claim 4, wherein treating the vaporized stream includes distilling the vaporized stream, wherein the treated stream is an overhead stream of the distillation.

6. A method, comprising:
vaporizing, in a vaporizer, a first liquid via heat transfer from a second liquid to form a vaporized stream that exits the vaporizer, the vaporized stream including monoethylene glycol (MEG);
increasing a pressure of the vaporized stream to form a pressurized vapor stream;
withdrawing a portion of the second liquid from the vaporizer, wherein the pressurized vapor stream has a dew point temperature higher than the portion of the second liquid;
increasing a temperature of the portion of the second liquid by transferring heat from the pressurized vapor stream to the portion of the second liquid in a thermal contactor without mixing the pressurized vapor stream with the portion of the second liquid, such that at least a portion of the pressurized vapor stream condenses in the thermal contactor; and returning the portion of the second liquid to the vaporizer after the increasing of the temperature of the portion of the second liquid.

7. The method of claim 6, wherein increasing the pressure of the vaporized stream includes:
   treating the vaporized stream to form a treated stream; and
   compressing the treated stream.

8. The method of claim 7, wherein treating the vaporized stream includes distilling the vaporized stream, wherein the treated stream is an overhead stream of the distillation.

9. The method of claim 6, further comprising adjusting a temperature of the pressurized vapor stream prior to transferring the heat from the pressurized vapor stream to the portion of the second liquid.

10. The method of claim 9, wherein adjusting the temperature of the pressurized vapor stream includes heating the pressurized vapor stream.

11. The method of claim 10, wherein heating the pressurized vapor stream includes vaporizing condensate formed by the increasing the pressure of the vaporized stream to form the pressurized vapor stream.

12. The method of claim 6, wherein the first liquid and the vaporized stream include water and MEG, and wherein increasing the pressure of the vaporized stream to form a pressurized vapor stream includes:
   distilling the vaporized stream to form a purified MEG stream; and
   increasing a pressure of the purified MEG stream to form the pressurized vapor stream.

13. The method of claim 1, wherein the first liquid includes MEG and the second liquid is immiscible with MEG.

14. The method of claim 1, wherein the first liquid and the second liquid are a same liquid that includes MEG.

15. The method of claim 1, wherein the pressurized vapor stream has a dew point temperature higher than the portion of the second liquid.

16. The method of claim 1, further comprising introducing the first liquid into the vaporizer before vaporizing the first liquid.

17. The method of claim 16, wherein the first liquid includes MEG and water.

18. The method of claim 6, wherein the first liquid includes MEG and the second liquid is immiscible with MEG.

19. The method of claim 6, wherein the first liquid and the second liquid are a same liquid that includes MEG.

* * * * *